United States Patent [19]
Wainwright

[11] Patent Number: 6,027,688
[45] Date of Patent: Feb. 22, 2000

[54] APPARATUS AND METHOD FOR INACTIVATION OF HUMAN IMMUNODEFICIENCY VIRUS

[75] Inventor: Basil E. Wainwright, Fort Lauderdale, Fla.

[73] Assignee: Polyatomic Apheresis, Ltd.

[21] Appl. No.: 08/237,713

[22] Filed: May 2, 1994

Related U.S. Application Data

[63] Continuation of application No. 07/922,532, Jul. 31, 1992, abandoned.

[51] Int. Cl.[7] .............................. A61L 2/20; A61M 1/36; B01J 19/12; C01B 13/11
[52] U.S. Cl. ..................... 422/28; 422/44; 422/186.08; 422/186.12; 422/186.14; 422/186.15; 422/186.18; 604/4; 435/2; 204/176
[58] Field of Search ........................... 422/44.28, 186.07, 422/176.08, 186.14, 186.18; 604/4.5; 435/2; 204/176

[56] References Cited

U.S. PATENT DOCUMENTS

| | | | |
|---|---|---|---|
| 3,727,612 | 4/1973 | Sayers et al. | 422/44 X |
| 4,314,344 | 2/1982 | Johns et al. | 204/176 X |
| 4,372,914 | 2/1983 | Raible | 435/2 X |
| 4,632,980 | 12/1986 | Zee et al. | 604/4 X |
| 4,986,968 | 1/1991 | Hirth et al. | 422/186.07 X |
| 5,052,382 | 10/1991 | Wainwright | 128/202.25 |

OTHER PUBLICATIONS

"The Use of Ozone in Medicine" by S. Rilling/R. Viebahn (Haug Publishers) (10 pages).
"Ozone Inactivates Extracellular Human Immunodeficiency Virus at Non–Cytoxic Concentrations" by Joel K. Freeberg and Michael T. Carpendale presented at IV International Conference on Aids in Stockholm, Sweden —Jun. 15–16, 1988.
"Inactication of Human Immunideficiency Virus Type 1 by Ozone in Vitro" by Keith H. Wells, Joseph Latino, Jerrie Gavalchin and Bernard J. Poiez —Blood, vol. 78, No. 7 (Oct. 1, 1991: pp. 1882–1890).

*Primary Examiner*—Elizabeth McKane
*Attorney, Agent, or Firm*—Dennis H. Lambert

[57] ABSTRACT

An apparatus and method for the inactivation of infectious organisms such as viruses, bacteria, fungi and protozoa, and especially for the inactivation of human immunodeficiency virus in proteinaceous material such as blood and blood products, without adversely affecting the normal physiological activity of the material, by contacting it for a time interval of only about 16 seconds with an ozone-oxygen mixture having an ozone concentration of only about 27 $\mu$/ml. The apparatus includes a gas-liquid contact apparatus through which the material and ozone-oxygen mixture flow in contacting, counter-current relationship, and an ozone generator which produces an ozone-oxygen mixture having a resonant frequency of about 7.83 Hz. The apparatus and method of the invention provide precise control of the concentration of ozone and the contact time between the material to be treated and the ozone-oxygen mixture.

24 Claims, 9 Drawing Sheets

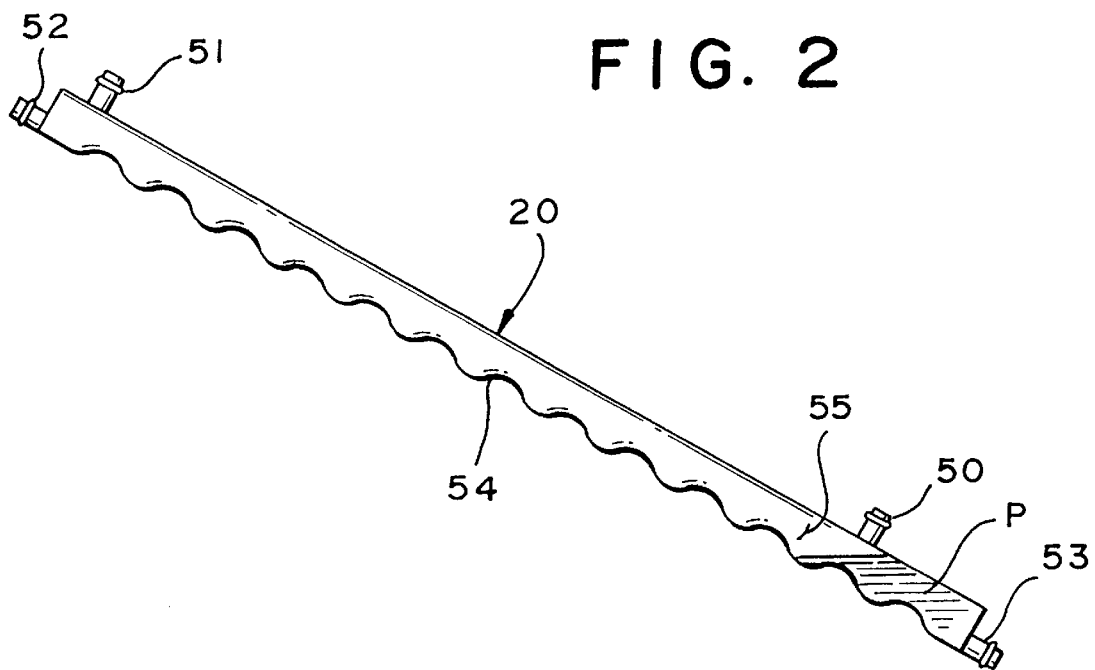
FIG. 2
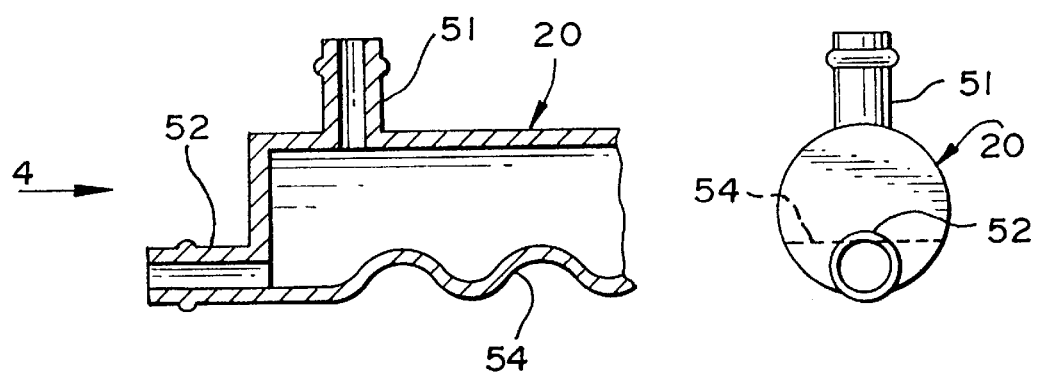
FIG. 3
FIG. 4

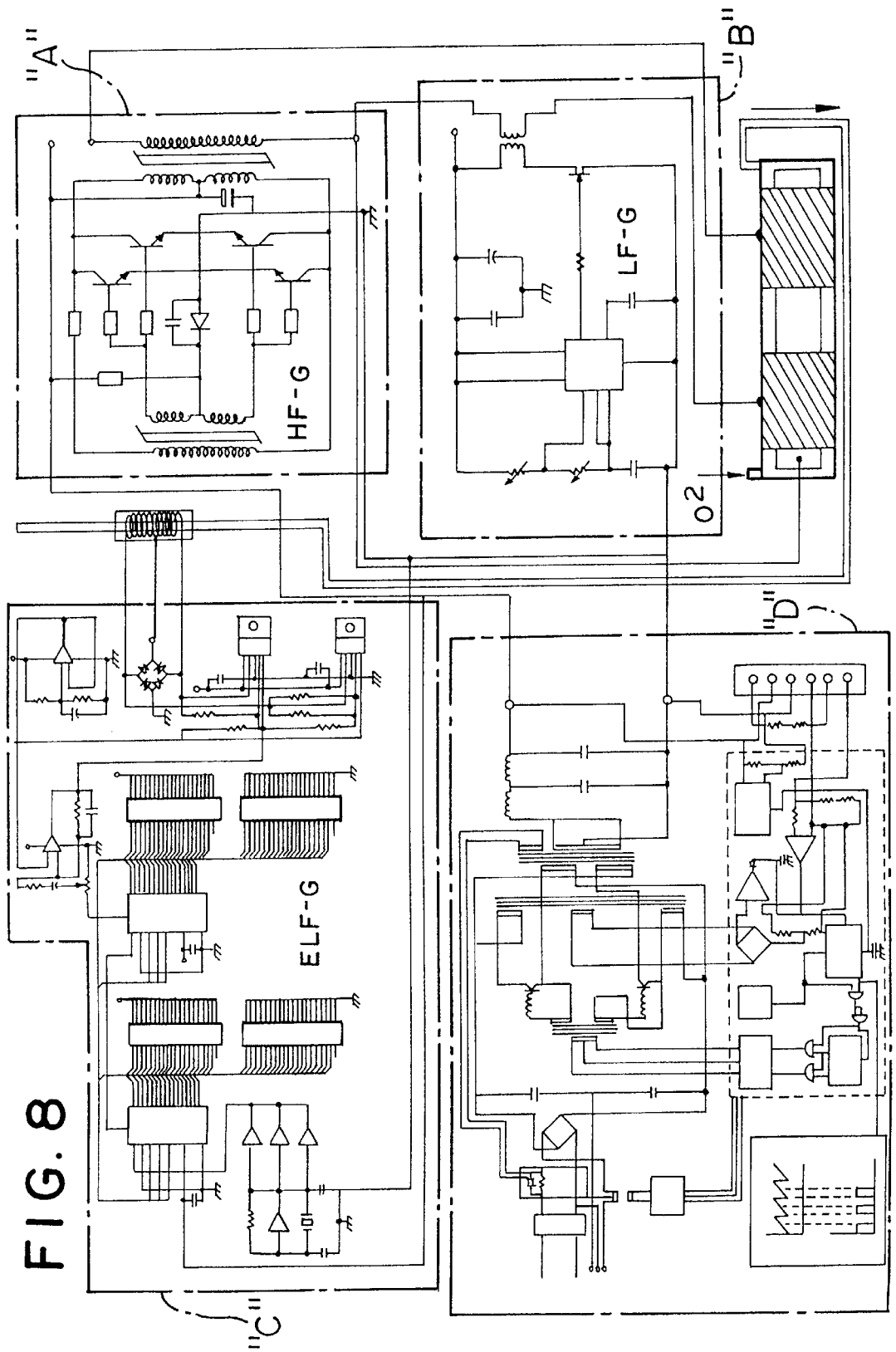

TRI-4: Transistor TIP 35C
D1: Diode IN5401
C1: Capacitor 1000mF 25v
C2: Capacitor 1mF 100v
R1-4: Resistor R47 2.5w
R5: Resistor 180r 1w
R6: Resistor 47r 11w
TX1: Drive Transformer FX3720
TX2: Output Transformer FX3750
Misc.: Heatsink for Transistors
: Tab Transistor Mounting Kit (4-off)
: Inverter P.C.B.

Circuit "A"

HFG

Circuit "B"

LFG

APPARATUS AND METHOD FOR INACTIVATION OF HUMAN IMMUNODEFICIENCY VIRUS

This application is a continuation of application Ser. No. 07/922,532, filed Jul. 31, 1992, now abandoned.

FIELD OF THE INVENTION

This invention relates to an apparatus and method for the treatment of blood and blood products to inactivate infectious organisms, such as viruses and bacteria, and especially to inactivate the human immunodeficiency virus (HIV) in human blood and blood products.

BACKGROUND OF THE INVENTION

Infectious diseases which once decimated entire populations are now largely controlled by modern drugs and sanitation methods. One virus, however, has remained elusive to medical science, and is infecting the human population in epidemic proportions. The human immunodeficiency virus (HIV), the etiologic agent of acquired immunodeficiency syndrome (AIDS), once generally regarded as a malady of homosexuals and intravenous drug abusers, has become a threat to all strata of society. In most instances, this virus leads to AIDS, and eventually death. Prior to the present invention, there was no known cure, nor were there any effective treatments for controlling the virus without causing unwanted side effects.

Some scientists believe that HIV may have been introduced into the human population through use of polio vaccines made from the tissue of infectious African green monkeys, many of which have been discovered to be infected with a retrovirus related to HIV. The rapid spread of this disease, however, is generally believed to be transmitted through infected blood and blood products, and through sexual contact. Drug abusers sharing used intravenous needles, persons receiving blood transfusions, and homosexuals and heterosexuals engaging in "unsafe" sexual contact are particularly vulnerable.

Intense efforts are being made to reduce the infectious risk of human blood products, and to control the spread of the virus among the human population.

Most efforts have been directed toward the development of drugs for controlling or killing the virus, but unlike most viruses, HIV becomes part of the genetic code of the cell. In order to kill the virus, it is necessary to destroy the cell. Moreover, the virus changes from individual to individual, and even within one person it can mutate in a matter of hours. This makes it virtually impossible to develop a drug specific to the virus, although some drugs, such as AZT, have shown promising results in neutralizing the virus. Unfortunately, AZT also produces serious side effects in many people because of its toxicity, and its use is therefore limited.

Because of these difficulties, other treatments have been tried or proposed, including thermal inactivation of viruses in blood derivatives, gamma-irradiation, porous membrane filtration, and solvent/detergent mixtures. However, these methods generally produce deleterious side effects and have achieved only limited success.

The prevailing view has been that by carefully screening blood and blood products to detect and eliminate contaminated materials, and by preventing the sharing of used needles among intravenous drug users, and by practising safe sex, the risk of transmission of the disease can be minimized. All of these methods are effective and do help reduce the rate of spread of the disease, but they do not offer a treatment or cure for the disease once a person becomes infected.

Moreover, lax and ineffectual screening of blood donors, and unreliable methods for detecting contaminated blood supplies, result in numerous instances of infected blood being made available for use in patients needing blood transfusions. Further, intravenous drug abusers generally do not pay heed to the dangers of sharing a needle; and passion, rather than prudence, usually controls sexual behavior.

Recent studies also indicate that the virus may be transmitted in ways other than previously believed. For instance, some scientists now believe that the HIV may be transmitted through mucous membranes, or even the skin. Dendritic cells move through the skin and mucous membranes searching for foreign proteins like bacteria and viruses. They pick up these foreign proteins and carry them to the lymph nodes, where T4 cells are stimulated to multiply and migrate into the blood to destroy the foreign invader. T4 cells are primed to die once they are infected, and over time the reduction in the number of T4 cells available to fight infection leads to collapse of the immune system.

Regardless of how the disease is transmitted, people are becoming infected at an alarming rate and an effective treatment is needed.

Ozone, the triatomic allotrope of oxygen, is a potent oxidant that has been shown to possess broad spectrum anti-microbial activity. It has been widely used in the treatment of sewage and in the purification of water, and was used medically in the treatment of wounds at least as early as World War I.

Advancements made by scientists in recent years using ozone to inactivate viruses, bacteria, fungi and protozoa have been well documented. It has reportedly been successfully used in several countries, most notably West Germany, in the treatment of AIDS, and specifically to inactivate HIV. In these treatments, ozone is generated from medically pure oxygen by electrical corona arc discharge. Blood from the patient being treated is then exposed to the ozone for a predetermined period of time, and at predetermined ozone concentrations to inactivate the virus.

In these prior art systems, the patient is treated with ozone by rectal insufflation, or by minor or major autohemotherapy. Much of the existing technology relies upon bubbling techniques to contact the blood or blood components with ozone/oxygen mixtures.

These methods offer inferior surface contact between the gas and blood, with little or no absorption controllability. Blood cells are also mechanically damaged by the bubbling techniques or porous membrane filters used in such methods, and it is difficult to control the concentrations of ozone necessary to inactivate the virus without adversely affecting normal biological and metabolic functions of the remaining blood components.

Further, treatment times are excessively long in prior art methods, taking up to eleven months for a full treatment protocol. This long treatment time makes conventional methods impractical for global treatment of the HIV epidemic. Moreover, excessively long treatment times cause discomfort and stress to the patient.

In addition, ozone is produced in accordance with prior art methods by using either low frequency (typically 50–60 Hz) or other, higher frequency generators. These methods of generation induce corresponding resonant frequencies in the ozone molecules, which, when exposed to the blood, expose the DNA to unnatural frequencies. Some research indicates that exposure to such frequencies can produce abnormal DNA activity and cell growth (cancer).

Consequently, even though ozone has shown promise in the inactivation of HIV, the shortcomings of prior art apparatus and methods have limited its use and hindered its acceptance as a viable medical tool.

There is thus need for an apparatus and method for using ozone in the treatment of blood contaminated with HIV, which enables accurate control over the process and in which treatment time is very short. Preferably, the apparatus and method should inactivate HIV but not adversely affect normal biological or metabolic activity in the blood, and should not involve the use of filters, bubblers, and the like, which can cause mechanical damage and trauma to the blood cells.

SUMMARY OF THE INVENTION

It is therefore an object of the present invention to provide an apparatus and method for using ozone in the treatment of blood and blood products, wherein precise control is maintained over the concentration of ozone, and blood-ozone exposure time is very short, so that infectious organisms are destroyed while normal biological and metabolic activities in the blood and blood products are not adversely affected.

Another object of the invention is to provide an apparatus and method for the inactivation of HIV by exposure of infected blood and/or blood products to ozone, in which mechanical damage to the blood and blood products is avoided.

A further object is to inactivate viruses, bacteria, fungi and protozoa by exposure of infected blood to ozone gas that has been produced with a generator operating at about 8 Hz, thereby approximating the natural resonant frequency of human biologic material.

Yet another object is to provide a new device for generating ozone from oxygen by using electric corona arc discharge, and then subjecting the ozone molecules to a low resonant frequency to approximate the natural resonant human biological frequency.

A still further object of the invention is to provide a device for counter flow of ozone gas and blood or blood products, in which substantially complete contact is made between the ozone gas and blood during a very short time period, without causing mechanical damage to the blood cells.

Yet another object is to provide an apparatus for gravity flow of blood or blood products in counter-current relationship with an ozone/oxygen gas mixture, in which the apparatus is automatically adjusted to maintain a constant flow rate to thereby insure a predetermined contact time between the ozone and blood; or which may be adjusted to different blood flow rates in dependence upon the characteristics of the blood and/or requirements of the patient.

These and other objects and advantages of the invention are achieved by a simple and relatively inexpensive apparatus which uses some commercially available components and some unique components in an extra-corporeal loop for the treatment of blood and other materials with precisely controlled concentrations of ozone over very short periods of time. Blood or blood products may be withdrawn from a patient or other source and caused to pass through the apparatus in a continuous process to destroy infectious agents in the blood or other material to be treated.

The apparatus preferably includes a mobile cart on which the treatment apparatus is mounted, so that it may be easily moved about. The treatment apparatus includes an oxygen tank containing medically pure oxygen that is supplied through a gas regulator to the ozone generator of the invention, where the oxygen is subjected to an electric corona arc discharge at a specific frequency to produce ozone. An ozone-oxygen mixture of precisely controlled concentration is then caused to flow from the ozone generator and upwardly through a gas-liquid contact apparatus, where the mixture makes thorough and intimate contact with a counter-flowing thin film of blood or other material to be treated flowing downwardly through the gas-liquid contact apparatus.

A pair of pumps may be operated proportionately, and the angle of inclination of the gas-liquid contact apparatus adjusted to achieve an essentially constant flow rate of blood through the contact apparatus, depending upon the consistency of the blood and the requirements of a particular patient.

The ozone generator of the invention comprises a tubular structure of silica glass or similar material, having an inlet for oxygen and an outlet for the ozone-oxygen mixture. In this generator, dual oscillators drive two sets of electrodes which alter the structure of oxygen and produce a mixture having predetermined proportions of $O_2$, $O_3$ and $O_4$. The mixture flowing from the ozone generator is subjected to a frequency of 7.83 Hz.

It has been found in experiments using the apparatus and methods of the invention that exposure of HIV-infected blood to an ozone-oxygen mixture having an ozone concentration of no more than about 27 $\mu$g/ml, or 2.0% by weight, and a surface pressure of about 2.2 psi, for a time period of only about sixteen seconds, resulted in inactivation of up to approximately 99% of the HIV, with no deleterious effect on cellular metabolism or DNA replication.

The invention is particularly adapted for the extra-corporeal treatment of human blood in a continuous process, wherein blood is withdrawn from a patient, circulated through the treatment apparatus of the invention and returned to the patient. Although the specific conditions of the treatment process may vary from patient to patient, depending upon the general health of the patient and the condition of the blood, satisfactory results are generally obtained when the blood is caused to flow through the gas-liquid contact apparatus at a flow rate of about 65 ml/min, typically achieved when the gas-liquid contact apparatus is inclined at an angle of about 27° to the horizontal, and the concentration of ozone in the ozone-oxygen mixture is no more than about 27 $\mu$g/ml and is at a surface pressure of about 2.2 psig.

The gas-liquid contact apparatus of the invention is non-foaming, whereby it is not necessary to reconstitute the blood after treatment, and treatment with the apparatus of the invention is virtually free of mechanical damage to blood components, especially in view of the variable onclusion pumps used to pump blood through the apparatus. Moreover, quick-connect/disconnect fittings are used to attach blood lines to the apparatus, whereby all components which might be contaminated with infected blood can be quickly and easily replaced between treatments, so that more treatments can be effected in a shorter amount of time than with conventional apparatus. The invention also provides means for detecting and proportionately adjusting blood flow rate and ozone concentration. Thus, if restriction to flow should occur, a flow sensor detects the reduction in flow and proportionately reduces the drive to the high and low frequency generators to thereby reduce the concentration of ozone.

BRIEF DESCRIPTION OF THE DRAWINGS

The foregoing and other objects and advantages of the invention will become apparent from the following detailed description when considered in conjunction with the accompanying drawings, wherein like reference characters designate like parts throughout the several views, and wherein:

FIG. 2 is an enlarged view in elevation of the unique cascade tube of the invention used to contact blood with ozone;

FIG. 3 is a further enlarged, fragmentary sectional view of a portion of the cascade tube of the invention;

FIG. 4 is an end view of the cascade tube of FIG. 3, looking in the direction of the arrow "4" in FIG 3;

FIG. 8 is a schematic circuit diagram of the means for energizing the coils in the ozone generator and for inducing a predetermined wave form and frequency of 7.83 Hz on the ozone generated by the ozone generator;

DETAILED DESCRIPTION OF THE PREFERRED EMBODIMENTS

Figure 1:
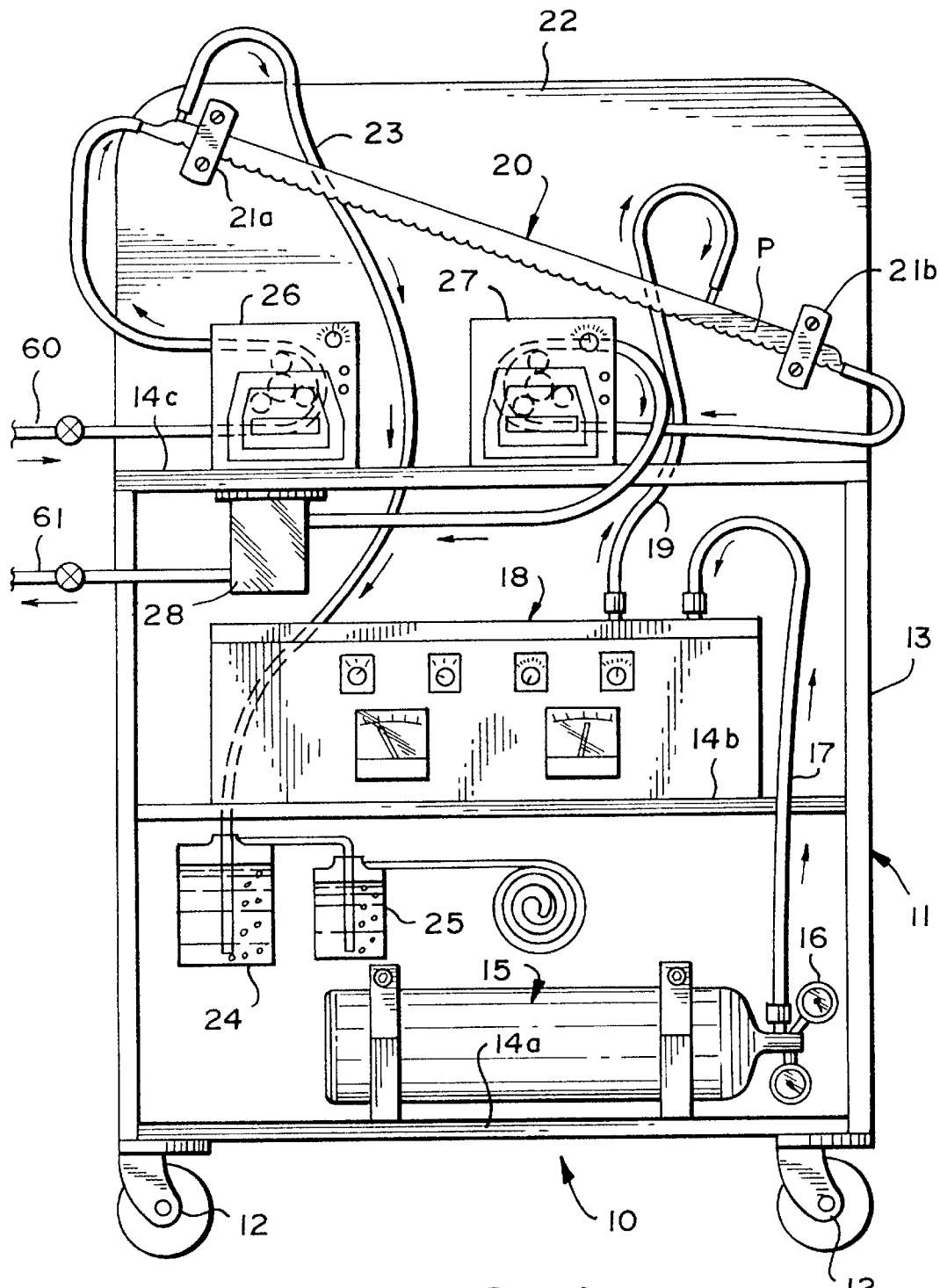
FIG. 1 is a view in elevation of an apparatus according to the invention.

Referring more specifically to the drawings, a blood treatment system in accordance with the invention is represented generally at 10 in FIG. 1.

In a preferred arrangement, the system 10 comprises a mobile cart 11 having wheels or casters 12 mounted on the bottom so that the cart can be easily moved about. The cart includes a frame 13 having three transversely mounted shelves 14a, 14b and 14c on which are supported the operative components of the invention.

An oxygen tank 15 is strapped on the bottom shelf 14a, and contains medically pure oxygen whose discharge is regulated through a conventional gas regulator valve assembly 16. A length of tubing 17 leads from the regulator 16 to an ozone generator 18 mounted on shelf 14b, where the oxygen is subjected to an electric corona arc discharge to produce ozone. An ozone-oxygen mixture from the ozone generator is then supplied via conduit 19 to the lower end of an inclined gas-liquid contact apparatus 20 supported on brackets 21a and 21b mounted on back plate 22. The ozone-oxygen mixture flows upwardly through the apparatus 20 to an outlet conduit 23 and thence to the atmosphere through a pair of serially connected ozone destructors 24 and 25, which permit variation in the back pressure imposed on the mixture.

Blood or other fluid to be treated is introduced through a first pump 26 into the upper end of the gas-liquid contact apparatus 20, for gravity flow downwardly through the apparatus in a cascading, thin film sheet to the lower end, where a pool P of the blood or other fluid is permitted to accumulate, and thence outwardly through a second pump 27 and filter 28 back to its source. Thorough and intimate contact between the ozone-oxygen mixture and blood occurs as they flow in counter-current relationship through the apparatus 20, thus exposing essentially all of the blood to the ozone-oxygen mixture.

The pumps 26 and 27 are preferably triple roller peristaltic pumps with adjustable onclusion. By minimizing the extent of onclusion exerted by the pumps on the tubing carrying the blood, the degree of potential mechanical damage to the blood cells can be minimized.

Ozone Generator

The ozone generator 18 comprises a pair of concentric tubes 30 and 31 of silica glass or other suitable material, connected and sealed at their adjacent ends to define an annular chamber 32 having an inlet 33 for oxygen and an outlet 34 for ozone-oxygen mixture. A first conductive sleeve or electrode 35 is disposed concentrically on the outer tube 31 at its inlet end, and a second conductive sleeve or electrode 36 is disposed concentrically on the outer tube 31 at its outlet end in axially spaced relationship to the first electrode.

Figure 10:
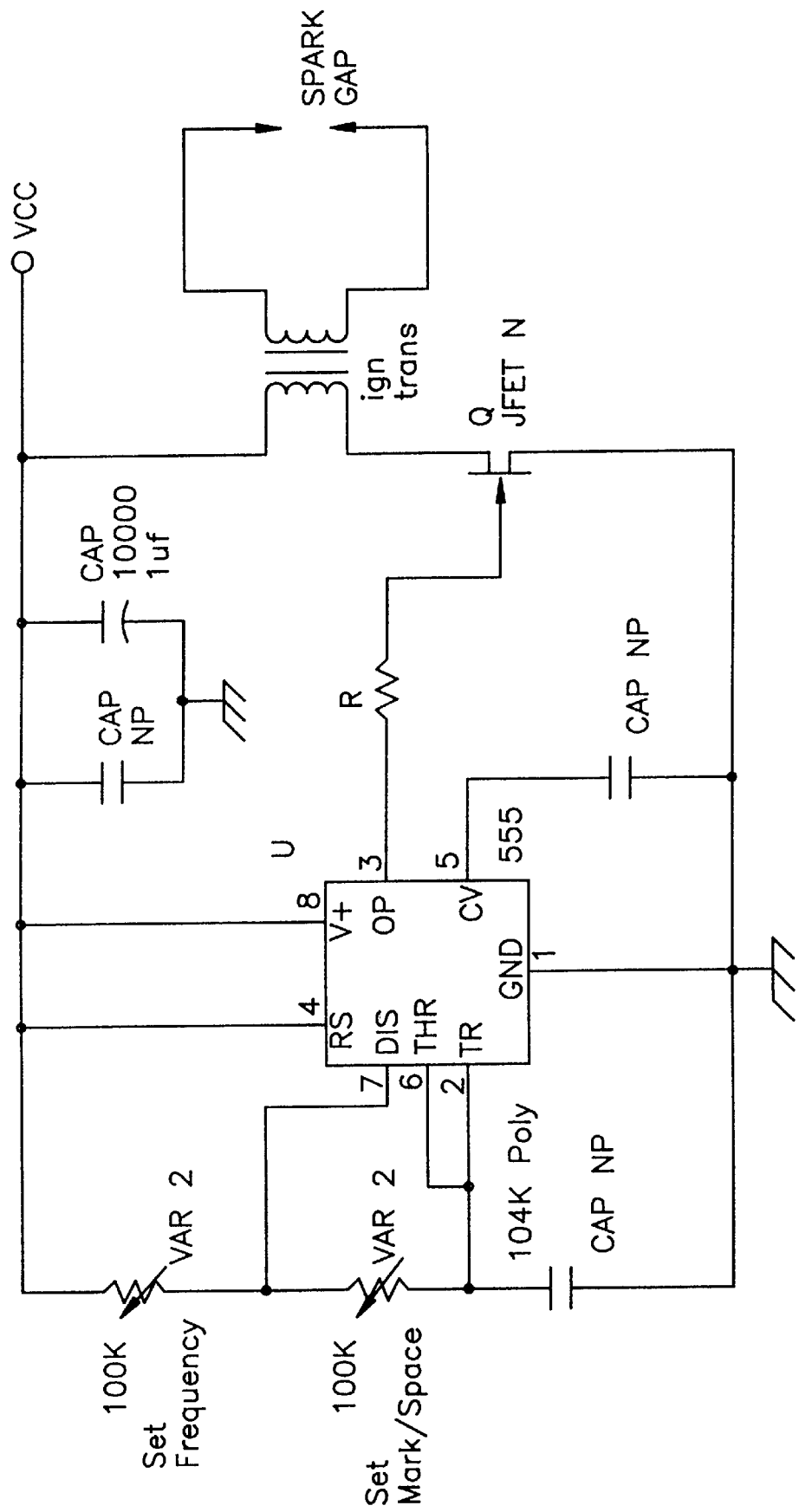
FIG. 10 is a schematic circuit diagram for the low frequency generator in FIG. 8.

The first electrode 35 is connected with the low frequency generator circuit B (see FIGS. 8 and 10) for producing a frequency of approximately 1.7 kilocycles on the gas as it enters the ozone generator to commence alteration of the incoming oxygen to $O_3$ and $O_4$.

The second electrode 36 is connected with the high frequency generator circuit A (see FIGS. 8 and 10) for producing a frequency of approximately 8.25 kilocycles on the $O_2$, $O_3$ and $O_4$ mixture as it leaves the silica cell, and stabilizes the $O_4$ component.

A third electrically conductive sleeve or electrode is disposed inside the inner tube 30 in concentric, radially inwardly spaced relationship to the two electrodes 35 and 36 and serves as a common ground.

The two tubes 30 and 31 and the annular space defined by them are thus located between the electrodes so that gas passing through the space is subjected to an electric corona arc discharge produced by the electrodes, converting oxygen to ozone.

The circuitry includes means for regulating the concentration of ozone produced in the silica cell, or generator, as determined by blood flow rate, preset values and other parameters. This may be accomplished by adjusting the flow rate of oxygen supplied to the ozone generator, and/or by adjusting the outputs of the high and low frequency generators.

The ozone-oxygen mixture produced in the ozone generator is subjected to an extremely low frequency in the range of about 7.83 Hz, developed by the swamp field generator circuit C of FIG. 8. This extremely low frequency generator controls the resonant molecular structure of the gas leaving the ozone generator. This circuit also minimizes undesireable field effects and spurious RF signals in the working environment.

The circuit is driven from an extremely stable power supply unit D, as shown in FIG. 8.

Figure 5:
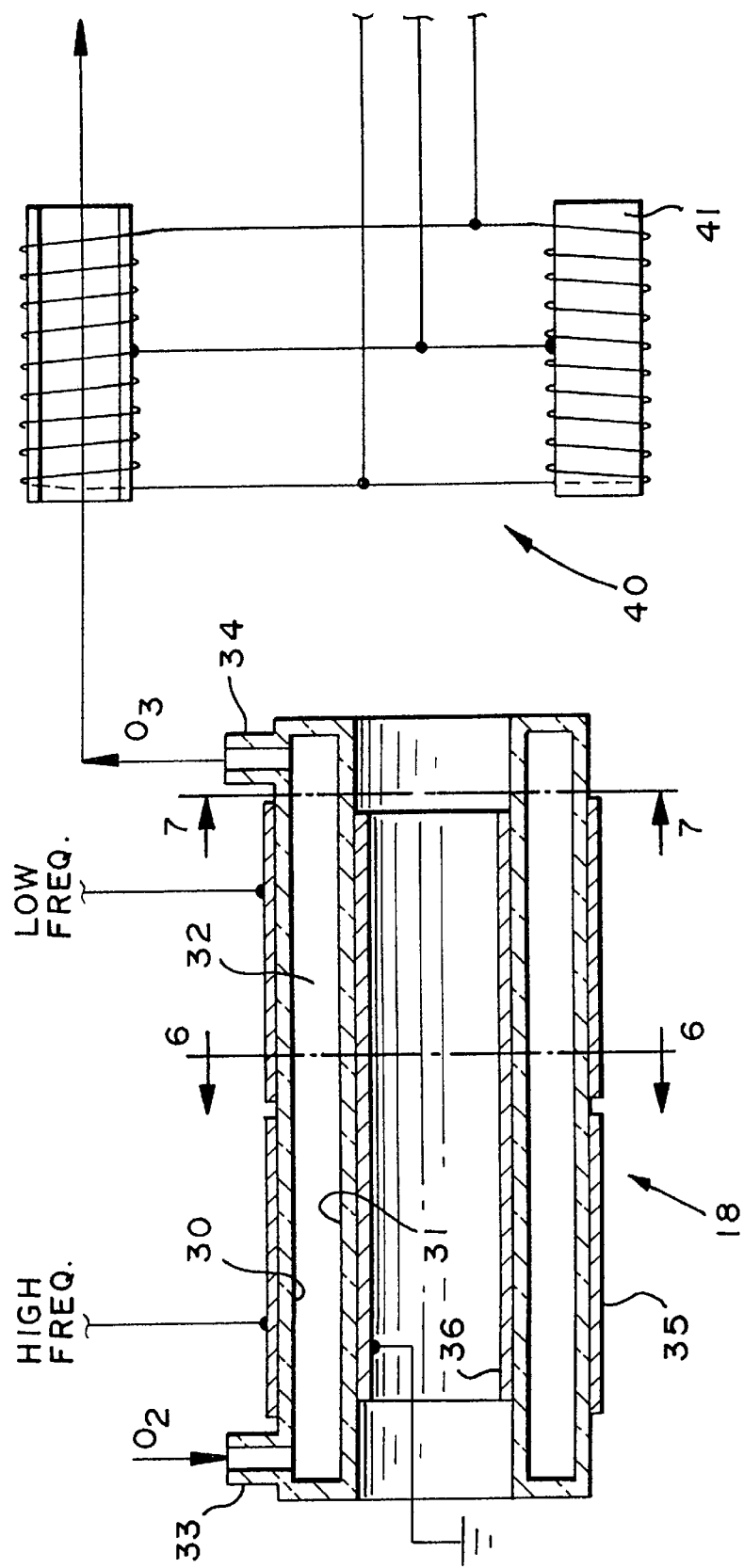
FIG. 5 is an enlarged longitudinal sectional view of the silica cell ozone generator according to the invention, with a portion of the apparatus for inducing a desired wave form and resonant frequency on the ozone molecules.
Figure 7:
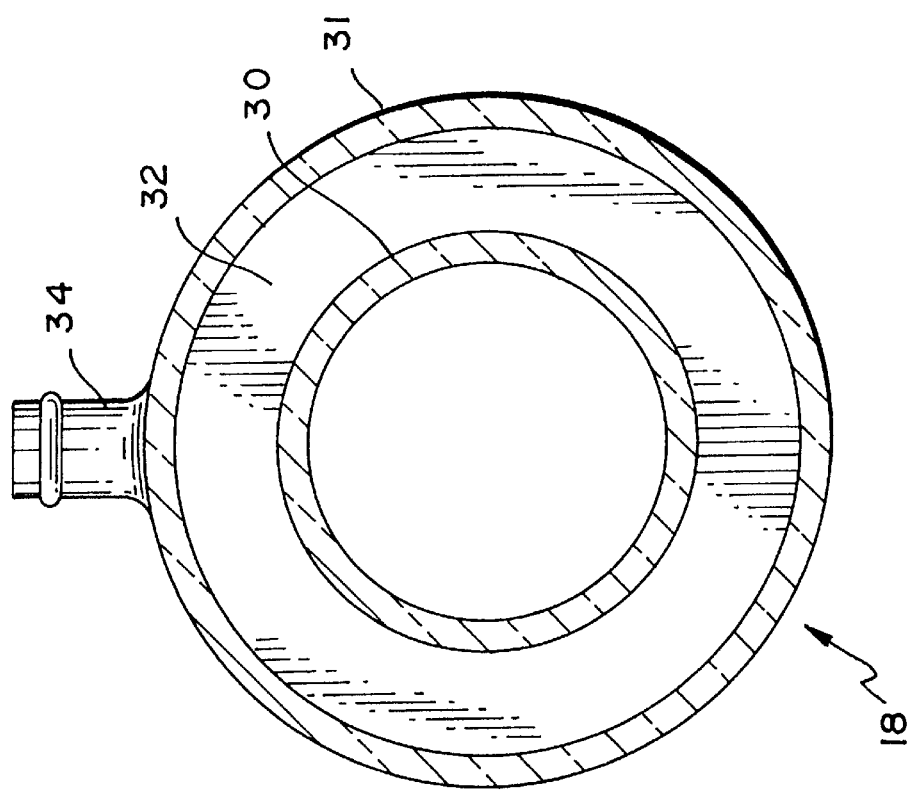
FIGS. 6 and 7 are transverse sectional views of the ozone generator of FIG. 5, taken along lines 6—6 and 7—7, respectively in FIG. 5.
Figure 6:
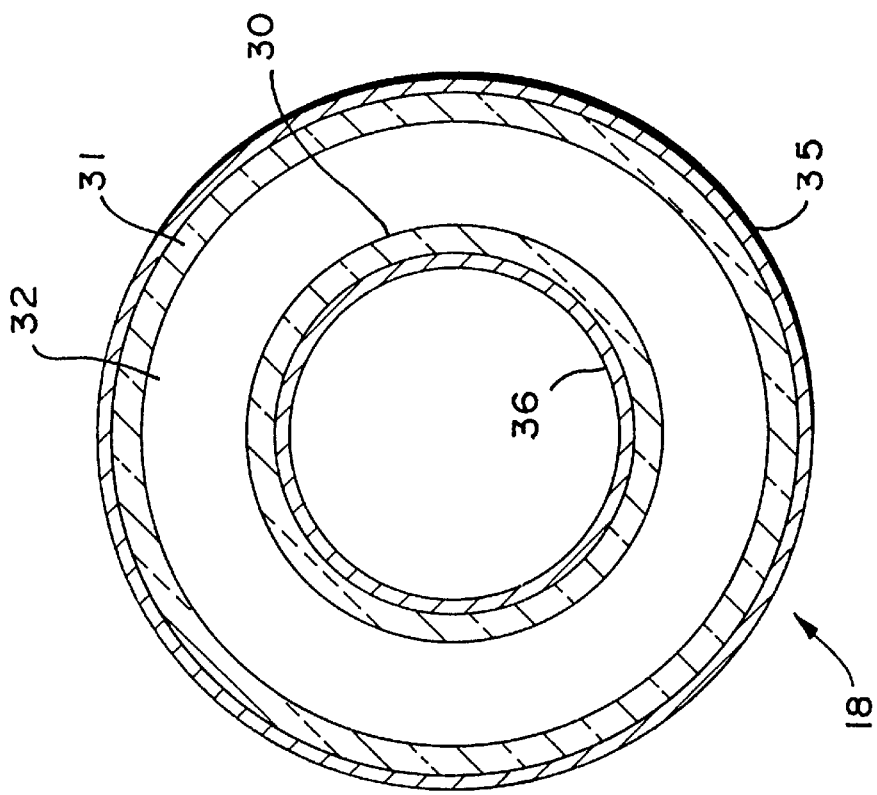
Figure 9:
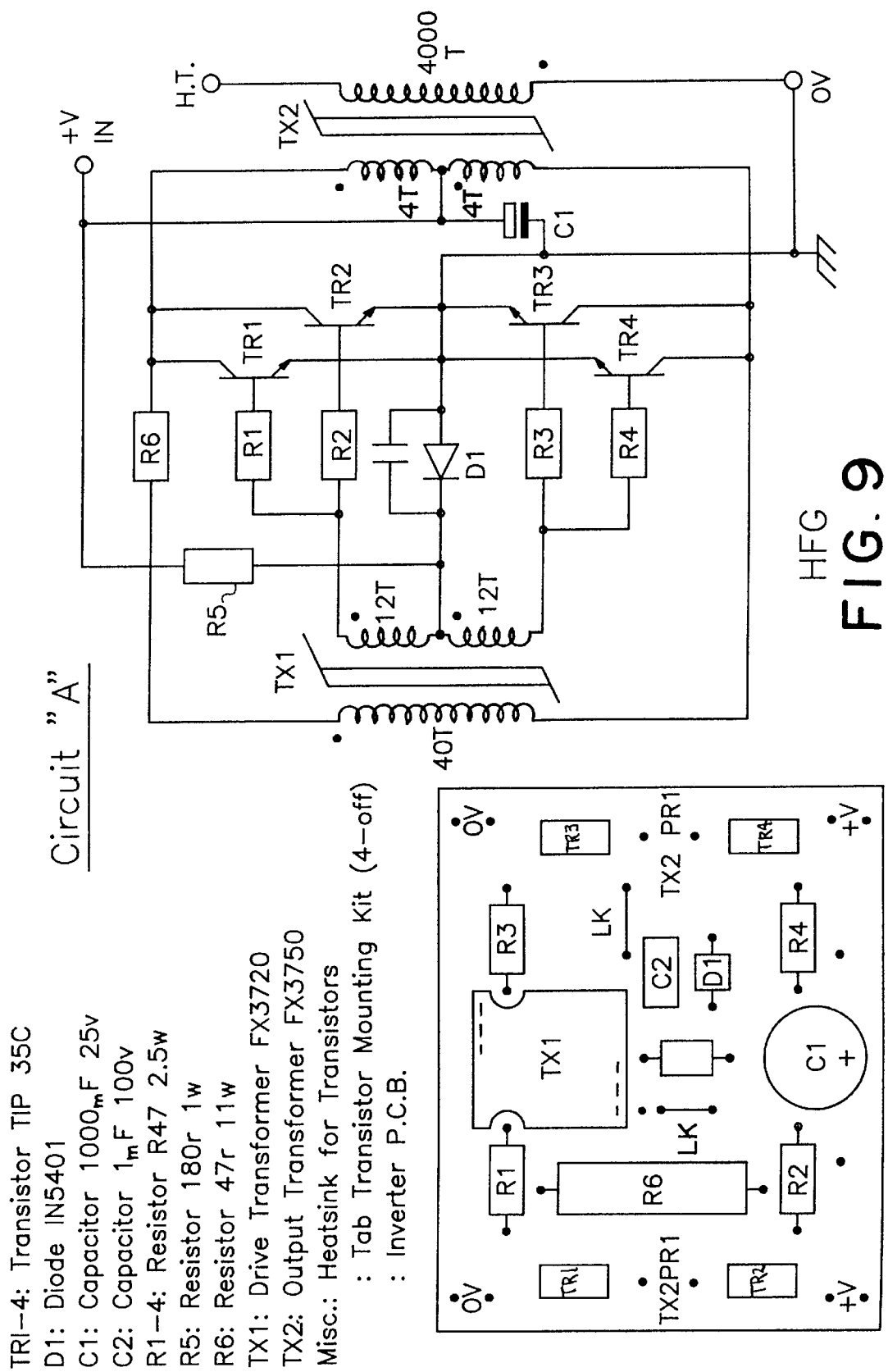
FIG. 9 is a schematic circuit diagram for the high frequency generator in FIG. 8.

As shown in FIGS. 5 and 8, for example, the swamp field generator 40 may comprise a laminated core 41 with oppositely wound coils thereon connected with complemental coils wound about the conduit carrying the ozone-oxygen mixture. These coils are energized from circuitry including the power supply unit D, connected through the 7.83 Hz generator, a push-pull phase lock loop generator and a driver power amp, further details of which are shown in FIGS. 8–11.

Figure 11:
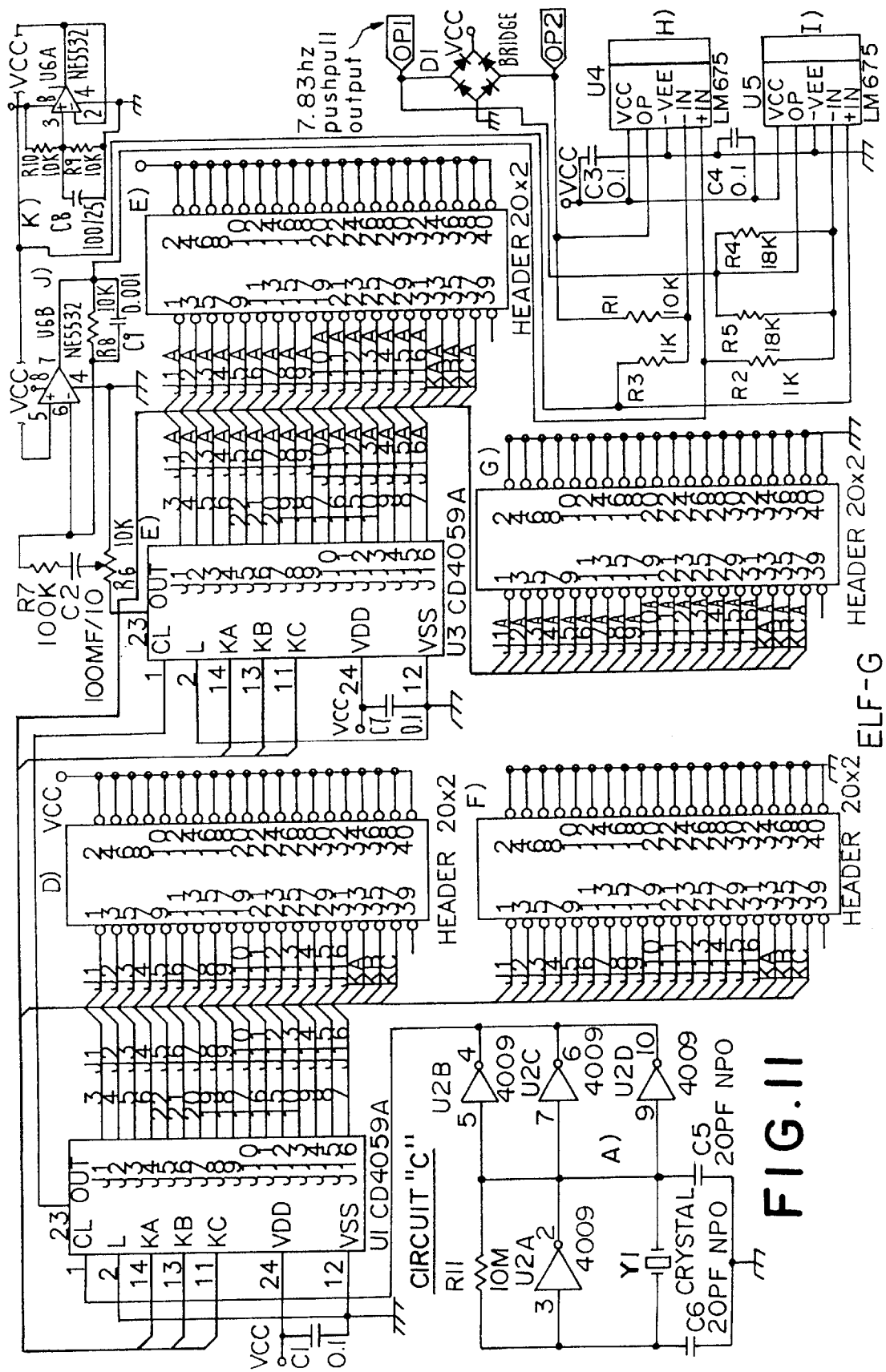
FIG. 11 is a schematic circuit diagram of the swamp field generator used in the circuit of FIG. 8 for minimizing undesireable field effects and spurious signals in the working environment.
Figure 12:
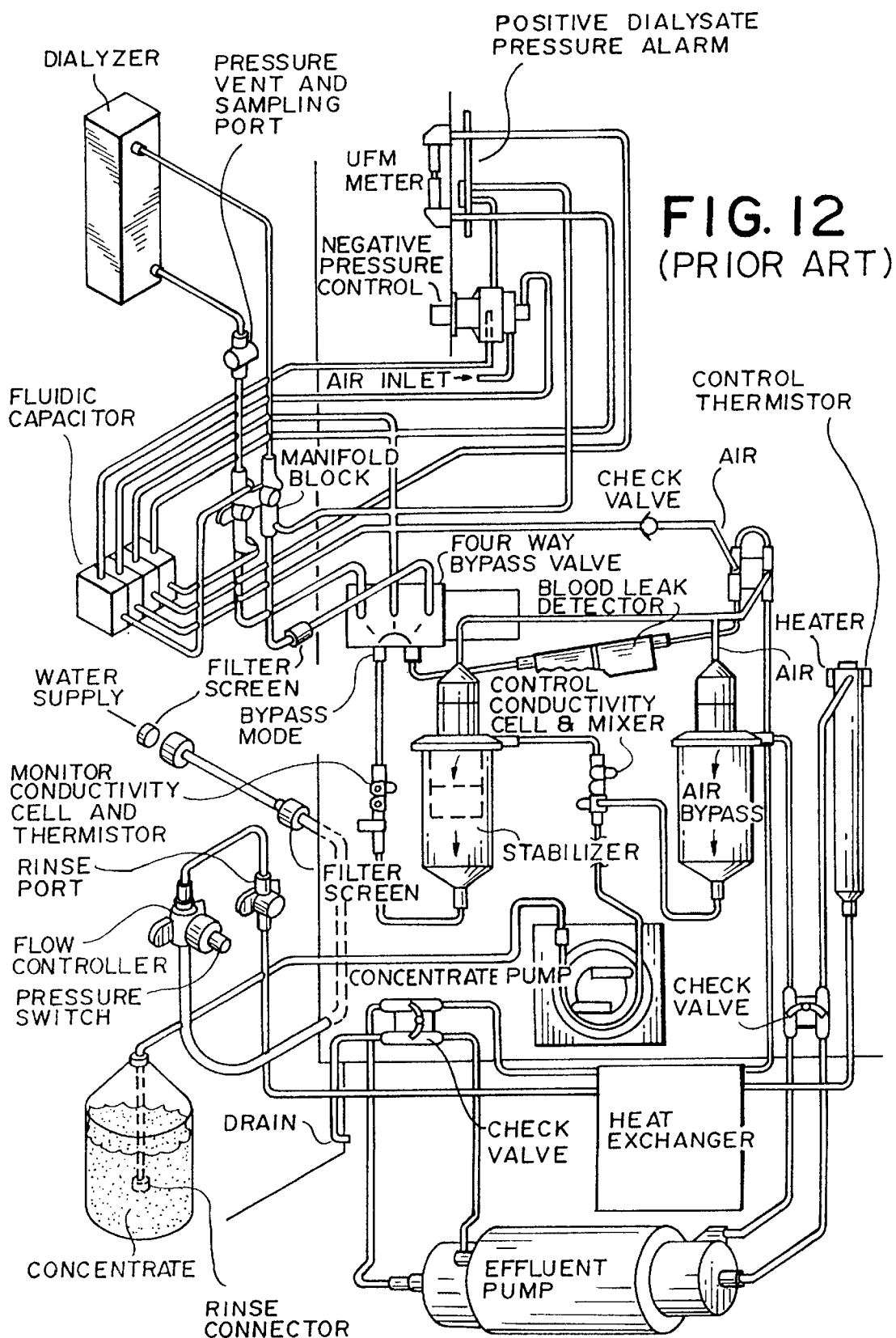
FIG. 12 is a schematic diagram of a typical dialysis system used in the prior art.

An example of suitable circuitry for generating a 7.83 Hz frequency signal is shown in FIG. 11 (circuit C), wherein a base frequency generator A is connected through first division pre-selectables B and C with jumper interface blocks D, E, P and G and operational amplifiers H and I to phase splitter J and central voltage generator K.

Gas-Liquid Contact Apparatus

The gas-liquid contact apparatus 20 comprises a length of Pyrex or glass tubing, preferably about 24 inches long and 20–25 mm in diameter, with a gas inlet fitting 50 in one side, spaced approximately 20 mm from one end, and a gas outlet fitting 51 in the same side of the tube but spaced about 20 mm from the other end. These fittings are each about 20 mm long and 7 mm in diameter.

Axially oriented and aligned inlet and outlet fittings 52 and 53, respectively, for flow of blood or other fluid into and from the tube are formed on opposite ends of the tube at its periphery on the side diametrically opposite that on which the gas fittings are provided. These fittings may be approximately the same size as the gas fittings previously described and are connected with conduits 60 and 61 (FIG. 1) for flow of blood or other material from and to a patient or other source.

The underside of the tube is formed with an undulating configuration 54, with the undulations having an amplitude of approximately 4 mm. These undulations define a relatively wide bottom surface over which the blood or other fluid spreads and tumbles as it cascades downwardly along the tube, creating a thin film of the fluid and exposing all parts of it to the gas passing in counter-current relationship through the tube.

The speed of operation of the pumps 26 and 27 may be proportionately adjusted so that a pool P of the blood or other fluid being treated forms in the lower end of the tube. This pool is permitted to form to a depth or level indicated by a mark 55 on the tube, or as sensed by a level sensor (not shown) provided in association with the tube. The level sensor may be connected through a suitable control means (not shown) to automatically adjust the pumps to maintain a desired level of fluid in the tube. This pool of fluid forms a liquid barrier or seal to prevent gas from escaping through the outlet 53.

Further, the angle of inclination of the tube may be adjusted to achieve a desired speed of flow of the blood or other fluid as it cascades down the undulating surface of the tube. For instance, fluids having different viscosity will flow at different speeds, and if blood is permitted to flow too slowly it may clot or coagulate. For instance, blood should flow through the tube 20 at a desired flow rate of about 65 milliliters per minute. To achieve this flow rate for fluids having different viscosity, or to adjust the flow rate to other values depending upon the requirements of a patient, one end 56 of the tube is pivotally supported on stanchion 22 and the other end is supported on stanchion 21 by an adjustment mechanism 57. This adjustment may be automatically accomplished by providing a flow rate detector (not shown) and suitable control means (not shown) responsive to the flow rate detector and operable to adjust the angle of inclination of the tube and/or to adjust the proportional speed of the pumps until the desired flow rate of blood or other fluid is obtained.

Other means, such as a densitometer or calorimeter 58, may be positioned to detect the condition of the blood or other fluid flowing from the tube 20, and connected through a suitable control means (not shown) to adjust the flow rate of the blood or other fluid and/or the flow rate and/or concentration of the ozone-oxygen mixture to maintain a desired condition of the blood or other fluid.

Although the invention is described herein as applied to the treatment of infectious diseases in humans, it should be understood that the principles of the invention are equally applicable to animals. Further, the invention could equally as well be applied to the treatment of blood supplies and to the extracorporeal treatment of patients.

While the invention has been illustrated and described in detail herein, it is to be understood that various modifications may be made therein without departing from the spirit and scope of the invention, as defined by the appended claims.

What is claimed is:

1. An apparatus for the treatment of blood, blood products and other materials to inactivate infectious organisms in the blood or other material, by contacting the blood, blood products or other material with a gaseous ozone-oxygen mixture, comprising:

a source of gaseous ozone-oxygen mixture;

a gas-liquid contact apparatus connected with the source of gaseous ozone-oxygen mixture and with a supply of the material to be treated, said gas-liquid contact apparatus comprising an elongate gas-liquid contact tube inclined to the horizontal and having first and second ends, with an inlet for the gaseous ozone-oxygen mixture in the first end and an outlet for the gaseous ozone-oxygen mixture in the second end so that the gaseous ozone-oxygen mixture flows through the tube from the first end to the second end, an inlet in the second end for the material to be treated, and an outlet in the first end for the material to be treated;

means for introducing the gaseous ozone-oxygen mixture and material to be treated to their respective inlets of the gas-liquid contact apparatus and for effecting gravity flow of the material to be treated from the second end to the first end of the tube, while the gaseous ozone-oxygen mixture is flowing from the first end to the second end of the tube in counter-current relationship to the flow of material to be treated and in contact therewith, said material to be treated forming a pool at said first end of the tube to preclude flow of the ozone-oxygen mixture through the outlet in the first end;

said gas-liquid contact tube have an undulating bottom surface over which the material to be treated flows in a thin film;

means for controlling the concentration of ozone in the gaseous ozone mixture, whereby the material to be treated is contacted with a predetermined concentration of ozone; and means for controlling the rate of flow of material to be treated so that it is exposed to the ozone-oxygen mixture for only about sixteen seconds while passing through the gas-liquid contact apparatus to inactivate infectious organisms but not to adversely affect the normal biologic activity of the material.

2. An apparatus as claimed in claim 1, wherein:

the concentration of ozone in the gaseous ozone-oxygen mixture is no more than about 27 μg/ml.

3. An apparatus as claimed in claim 1, wherein:
the surface pressure of the gaseous ozone-oxygen mixture in the gas-liquid contact tube is no more than about 2.2 psig.

4. An apparatus as claimed in claim 1, wherein:
the source of gaseous ozone-oxygen mixture is an ozone generator which produces ozone from medically pure oxygen by electric corona arc discharge; and
means is operatively associated with said ozone generator to impose a resonant frequency of about 7.83 Hz on the ozone molecules.

5. An apparatus as claimed in claim 4, wherein:
the ozone generator comprises an elongate inner tube of non-conductive inert material, and an elongate outer tube of non-conductive inert material in concentric, radially outwardly spaced relationship to the inner tube, said tubes being connected and sealed at their adjacent ends to define an annular chamber;
an inlet for medically pure oxygen at one end of the chamber, said inlet connected with a source of medically pure oxygen, and an outlet for ozone-oxygen mixture at the other end of the chamber;
electrically conductive means disposed on the outside of the outer tube and on the inside of the inner tube, said electrically conductive means being connected with electrical circuit means to produce an electric corona arc discharge in the chamber to produce ozone from the oxygen supplied to the chamber; and
flow control means connected with the source of oxygen to regulate the flow of oxygen supplied to the chamber to regulate the concentration of ozone-oxygen in the gaseous ozone mixture produced in the chamber.

6. An apparatus as claimed in claim 1, wherein:
means is operatively associated with the gaseous ozone-oxygen mixture supplied to the gas-liquid contact tube for imposing a resonant frequency of about 7.83 Hz on the gaseous ozone-oxygen mixture.

7. An apparatus as claimed in claim 1, wherein:
means is operatively associated with the gaseous ozone-oxygen mixture supplied to the gas-liquid contact tube for imposing a resonant frequency of about 7.83 Hz on the gaseous ozone-oxygen mixture, said means comprising a coil disposed around the path of the gaseous ozone-oxygen mixture prior to it entering the chamber, a steady state electric power source, and frequency generator means connected with the power source and with the coil for inducing a frequency of about 7.83 Hz on the coil and thus on the gaseous ozone-oxygen mixture passing therethrough.

8. An apparatus as claimed in claim 7, wherein:
the concentration of ozone in the gaseous ozone-oxygen mixture is no more than about 27 µg/ml.

9. An apparatus as claimed in claim 8, wherein:
the means for introducing and controlling the rate of flow of the gaseous ozone-oxygen mixture and material to be treated in the gas-liquid contact tube are operable to effect a time of contact between the gaseous ozone-oxygen mixture and the material being treated of only about 16 seconds.

10. An apparatus as claimed in claim 9, wherein:
the surface pressure of the gaseous ozone-oxygen mixture in the gas-liquid contact tube is no more than about 2.2 psig.

11. An apparatus as claimed in claim 10, wherein:
the source of gaseous ozone-oxygen mixture is an ozone generator which produces ozone from medically pure oxygen by electric corona arc discharge.

12. An apparatus as claimed in claim 11, wherein:
the ozone generator comprises an elongate inner tube of non-conductive inert material, and an elongate outer tube of non-conductive inert material in concentric, radially outwardly spaced relationship to the inner tube, said tubes being connected and sealed at their adjacent ends to form an annular chamber;
an inlet for medically pure oxygen at one end of the chamber, said inlet connected with a source of medically pure oxygen, and an outlet for ozone-oxygen mixture at the other end of the chamber;
electrically conductive means disposed on the outside of the outer tube and on the inside of the inner tube, said electrically conductive means being connected with electrical circuit means to produce an electric corona arc discharge in the chamber to produce ozone from the oxygen supplied to the chamber; and
flow control means connected with the source of oxygen to regulate the flow of oxygen supplied to the chamber to regulate the concentration of ozone in the gaseous ozone-oxygen mixture produced in the chamber.

13. A gas-liquid contact apparatus for contacting blood, blood products and other liquid material to be treated with a gaseous ozone-oxygen mixture to inactivate infectious organisms in the blood or other material without adversely affecting normal metabolic functions of the material, comprising:
an elongate tube of inert material, said tube having first and second ends;
an inlet in the first end and an outlet in the second end for a gaseous ozone-oxygen mixture;
an inlet in the second end and an outlet in the first end for blood or other material to be contacted with the gaseous ozone-oxygen mixture;
means for introducing blood or other material at a predetermined flow rate into the inlet in the second end;
means supporting said tube at an angle of inclination with respect to horizontal to effect a thin film, gravity flow through the tube of said blood or other material;
means for controlling the flow rate of the blood or other material so that a pool of blood or other material forms in the tube at the outlet in the first end, forming a liquid seal at said outlet to prevent the flow of gaseous ozone-oxygen mixture therethrough; and
means for introducing an ozone-oxygen mixture into the inlet in the first end at a controlled, predetermined ozone concentration and causing it to flow through the tube in counter-current, contacting relationship with the blood or other material.

14. A gas-liquid contact apparatus as claimed in claim 13, wherein:
the tube has a generally circular transverse cross-sectional shape and in use has a bottom side;
said bottom side being formed with a plurality of indentations or undulations extending along the length of the tube to cause blood or other material to cascade or tumble as it flows through the tube, thereby exposing essentially all of the material to the ozone-oxygen mixture flowing in counter-current relationship thereto.

15. A gas-liquid contact apparatus as claimed in claim 14, wherein:
the means supporting said tube is adjustable to vary the angle of inclination of the tube for thereby varying the flow rate of the blood or other material flowing therethrough.

16. An apparatus for the treatment of blood, blood products and other materials to inactivate infectious organisms in the blood or other material, comprising:

an ozone generator for generating a gaseous ozone-oxygen mixture, said ozone generator having an elongate inner tube of non-conductive inert material, and an elongate outer tube of non-conductive inert material in concentric, radially outwardly spaced relationship to the inner tube, said tubes being connected and sealed at their adjacent ends to form an annular chamber;

an inlet for medically pure oxygen at one end of the chamber, said inlet connected with a source of medically pure oxygen, and an outlet for ozone-oxygen mixture at the other end of the chamber;

electrically conductive means disposed on a radially outer surface of the outer tube and on a radially inner surface of the inner tube, said electrically conductive means being connected with electrical circuit means to produce an electric corona arc discharge in the chamber to produce ozone from the oxygen supplied to the chamber;

flow control means connected with the source of oxygen to regulate the flow of oxygen supplied to the chamber to regulate the concentration of ozone in the gaseous ozone-oxygen mixture produced in the chamber;

a gas-liquid contact apparatus connected with the ozone generator to receive the ozone-oxygen mixture produced therein, and connected with a supply of material to be treated, said gas-liquid contact apparatus comprising a tube inclined to the horizontal and having an inlet and an outlet for the ozone-oxygen mixture, and an inlet and an outlet for the material to be treated, said inlets and outlets being arranged for counter-current, contacting flow of the ozone-oxygen mixture and the material to be treated as they pass through the gas-liquid contact apparatus, said inclined tube having an inner surface over which the material flows in a thin film as it passes therethrough under gravity flow; and means for controlling the rate of flow of material to be treated as it passes through the gas-liquid contact apparatus, whereby the material to be treated is contacted with a predetermined concentration of ozone for a predetermined time interval to inactivate infectious organisms but not to adversely affect the normal biologic activity of the material.

17. An apparatus as claimed in claim 16, wherein:

means is operatively associated with the ozone-oxygen mixture supplied from the ozone generator for imposing a resonant frequency of about 7.83 Hz on the ozone-oxygen mixture, said means comprising a coil disposed around the path of the ozone-oxygen mixture as it leaves the ozone generator, a steady state electric power source, and frequency generator means connected with the power source and with the coil for inducing a frequency of about 7.83 Hz on the coil and thus on the ozone-oxygen mixture passing therethrough.

18. An apparatus as claimed in claim 17, wherein:

the gas-liquid contact apparatus comprises an elongate tube of inert material, said tube having first and second ends;

an inlet in the first end and an outlet in the second end for the ozone-oxygen mixture;

an inlet in the second end and an outlet in the first end for blood or other material to be treated;

means for introducing blood or other material at a predetermined flow rate into the inlet in the second end;

means supporting said tube at a predetermined angle of inclination with respect to horizontal to effect a thin film, gravity flow through the tube of said blood or other material; and means for introducing an ozone-oxygen mixture into the inlet in the first end at a controlled, predetermined ozone concentration and causing it to flow through the tube in counter-current, contacting relationship with the blood or other material.

19. An apparatus as claimed in claim 18, wherein:

the tube has a generally circular transverse cross-sectional shape and in use has a bottom side;

said bottom side being formed with a plurality of indentations or undulations extending along the length of the tube to cause blood or other material to cascade or tumble as it flows through the tube, thereby exposing essentially all of the material to the ozone-oxygen mixture flowing in counter-current relationship thereto.

20. A gas-liquid contact apparatus as claimed in claim 19, wherein:

the means supporting said tube is adjustable to vary the angle of inclination of the tube for thereby varying the flow rate of the blood or other material flowing therethrough.

21. A method of inactivating the human immunodeficiency virus in proteinaceous material without adversely affecting the normal physiological activity of the material, by contacting the material for a short time interval with an ozone-oxygen mixture having a low concentration of ozone, comprising the steps of:

generating ozone from medically pure oxygen by electric corona arc discharge in an ozone generator to produce an ozone-oxygen mixture;

controlling the concentration of ozone in the mixture to no more than about 27 $\mu$g/ml by regulating the flow of oxygen to the ozone generator;

causing gravity flow in a thin film of the proteinaceous material through a gas-liquid contact apparatus;

controlling the flow rate of the proteinaceous material so that it passes through the gas-liquid contact apparatus in about 16 seconds; and causing the ozone-oxygen mixture to flow through the gas-liquid contact apparatus in contacting, counter-current relationship to the proteinaceous material so that essentially all of the material is contacted with the ozone-oxygen mixture.

22. A method as claimed in claim 21, including the step of:

causing the proteinaceous material to tumble or cascade as it passes through the gas-liquid contact apparatus to insure exposure of essentially all of the material to the ozone-oxygen mixture as the material and mixture pass through the gas-liquid contact apparatus.

23. A method as claimed in claim 22, including the step of:

imposing a resonant frequency of about 7.83 Hz on the ozone-oxygen mixture prior to passing it through the gas-liquid contact apparatus.

24. An ozone generator for producing ozone gas from medically pure oxygen, comprising:

an elongate inner tube of non-conductive inert material, and an elongate outer tube of non-conductive inert material in concentric, radially outwardly spaced relationship to the inner tube, said tubes being connected and sealed at their adjacent ends to form an annular chamber;

an inlet for medically pure oxygen at one end of the chamber, said inlet connected with a source of medically pure oxygen, and an outlet for ozone-oxygen mixture at the other end of the chamber;

electrically conductive means disposed on the outside of the outer tube and on the inside of the inner tube, said electrically conductive means being connected with electrical circuit means to produce an electric corona arc discharge in the chamber to produce ozone from the oxygen supplied to the chamber;

flow control means connected with the source of oxygen to regulate the flow of oxygen supplied to the chamber to regulate the concentration of ozone in the gaseous ozone-oxygen mixture produced in the chamber; and means operatively associated with the gaseous ozone-oxygen mixture supplied from the ozone generator for imposing a resonant frequency of about 7.83 Hz on the gaseous ozone-oxygen mixture, said means comprising a coil disposed around the path of the gaseous ozone-oxygen mixture as it leaves the ozone generator, a steady state electric power source, and frequency generator means connected with the power source and with the coil for inducing a frequency of about 7.83 Hz on the coil and thus on the gaseous ozone-oxygen mixture passing therethrough.

* * * * *